United States Patent [19]

Möhring et al.

[11] 4,326,086
[45] Apr. 20, 1982

[54] PROCESS FOR THE PREPARATON OF LOW MOLECULAR WEIGHT POLYHYDROXYL COMPOUNDS

[75] Inventors: Edgar Möhring, Bergisch-Gladbach; Hanns P. Müller; Kuno Wagner, both of Leverkusen, all of Fed. Rep. of Germany

[73] Assignee: Bayer Aktiengesellschaft, Leverkusen, Fed. Rep. of Germany

[21] Appl. No.: 934,650

[22] Filed: Aug. 17, 1978

[30] Foreign Application Priority Data

Aug. 24, 1977 [DE] Fed. Rep. of Germany ....... 2738154

[51] Int. Cl.$^3$ ..................... C07C 27/00; C07C 31/18; C07C 45/45
[52] U.S. Cl. .................................. 568/388; 568/463; 568/863; 521/158; 528/77; 528/85
[58] Field of Search ...................... 568/863, 463, 388; 260/594, 602

[56] References Cited

U.S. PATENT DOCUMENTS

| | | | |
|---|---|---|---|
| 2,224,910 | 12/1940 | Hanford et al. | 260/594 |
| 2,269,935 | 1/1942 | Hanford et al. | 260/594 |
| 2,760,983 | 8/1956 | MacLean et al. | 260/594 |
| 2,775,621 | 12/1956 | MacLean et al. | 568/863 |

*Primary Examiner*—Joseph E. Evans
*Attorney, Agent, or Firm*—Gene Harsh; Joseph C. Gil

[57] ABSTRACT

This invention relates to an improved process for the preparation of formose by the condensation of aqueous formaldehyde. In the process according to this invention, tertiary amines which contain an electrophilic hetero atom in the β-position to the tertiary nitrogen atom are used for controlling the pH instead of the inorganic bases which have previously been used for this purpose.

1 Claim, No Drawings

PROCESS FOR THE PREPARATON OF LOW MOLECULAR WEIGHT POLYHYDROXYL COMPOUNDS

BACKGROUND OF THE INVENTION

"Formose" is a term used to define the known mixtures of low molecular weight polyhydroxyl compounds (polyhydric alcohols, hydroxyaldehydes and hydroxyketones) which are formed by the condensation of formaldehyde hydrate.

The preparation of mixtures of polyhydric alcohols, hydroxyaldehydes and hydroxyketones by the autocondensation of formaldehyde hydrate has been described in several publications in the literature. The following are examples of relevant literature references: Butlerow and Loew, Annalen 120, 295 (1861); J.pr.Chem, 33, 321 (1886); Pfiel, chemische Berichte 84, 229 (1951); Pfeil and Schroth, chemische Berichte 85, 303 (1952); R. D. Partridge and A. H. Weiss, Carbohydrate Research 24, 29–44 (1972); the formoses of glyceraldehyde and dihydroxyacetone according to Emil Fischer; German Pat. Nos. 822,835, 830,951 and 884,794; U.S. Pat. Nos. 2,224,910; 2,269,935; and 2,272,378 and British Pat. No. 513,708. These known processes, however, involve certain disadvantages such as toxicologically harmful catalysts, low volume/time yields and discolored by-products. New processes by which formoses which are virtually colorless and free from undesirable by-products can be obtained in high yields with the aid of conventional catalysts have recently been developed.

According to one of these new processes, the condensation of formaldehyde hydrate is carried out in the presence of a catalyst consisting of a soluble or insoluble lead (II) salt, or of lead (II) ions bound to a high molecular weight carrier, and in the presence of a cocatalyst consisting of a mixture of hydroxyaldehydes and hydroxyketones of the kind which is obtained from the condensation of formaldehyde hydrate and which is characterized by the following molar ratios:

| |
|---|
| Compounds with 3 carbon atoms/ compounds with 4 carbon atoms: 0.5:1 to 2.0:1; |
| Compounds with 4 carbon atoms/ compounds with 5 carbon atoms: 0:2:1 to 2.0:1; |
| Compounds with 5 carbon atoms/ compounds with 6 carbon atoms: 0.5:1 to 5.0:1. |

In these mixtures the proportion of components with 3 to 6 carbon atoms is at least 75% by weight, preferably more than 85% by weight, based on the whole cocatalyst. The reaction temperature used is generally between 70° and 110° C., preferably between 80° and 100° C., and the pH of the reaction solution is adjusted by controlled addition of a base, first to a value of from 6.0 to 8.0, preferably from 6.5 to 7.0, until 10 to 60%, preferably 30 to 50% conversion has been reached, and thereafter to a value of from 4.0 to 6.0, preferably from 5.0 to 6.0. It has surprisingly been found that the proportion of components in the mixtures of polyols, hydroxyaldehydes and hydroxyketones obtained could be varied in a reproducible manner by this special method of pH control followed by cooling at different residual formaldehyde contents of 0 to 10% by weight, preferably 0.5 to 6% by weight.

When the autocondensation of formaldehyde hydrate has been stopped by cooling and/or by inactivation of the lead catalyst with acids, the catalyst may be removed in known manner and the water contained in the product is evaporated off. Further details of this process may be found in German Offenlegungsschrift No. 2,639,084.

According to another method of preparing highly concentrated, colorless formoses in high volume/time yields, aqueous formalin solutions and/or para-formaldehyde dispersions are condensed in the presence of a soluble or insoluble metal catalyst and in the presence of a cocatalyst which has been obtained by the partial oxidation of a dihydric or polyhydric alcohol with a molecular weight of 62 to 242 and containing at least two vicinal hydroxyl groups, or a mixture of such alcohols. During this reaction the pH of the reaction solution is maintained between 6.0 and 9.0 by controlled addition of a base up to 5 to 40% conversion. The pH of the reaction mixture is thereafter adjusted to 4.5 to 8.0 until termination of the condensation reaction. During this second reaction phase, the pH is 1.0 to 2.0 units lower than during the first reaction phase. The reaction is then stopped at a residual formaldehyde content of from 0 to 10% by weight by inactivation of the catalyst. The catalyst is then removed. This method has been described in German Offenlegungsschrift No. 2,718,084.

High grade formoses can also be obtained by the condensation of formaldehyde in the presence of a metal catalyst and more than 10% by weight, based on the formaldehyde, of one or more dihydric or polyhydric low molecular weight alcohols and/or higher molecular weight polyhydroxyl compounds. Such formose-polyol mixtures are the subject matter of German Offenlegungsschrift No. 2,714,104.

It is particularly economical to produce formose directly from synthesis gases containing formaldehyde, i.e. without first preparing aqueous formalin solutions or paraformaldehyde. The synthesis gases obtained from the large scale industrial production of formaldehyde are introduced continuously or discontinuously at temperatures of between 10° and 150° C. into an absorption liquid consisting of water, monohydric or polyhydric low molecular weight alcohols, and/or higher molecular weight polyhydroxyl compounds. Compounds capable of enediol formation may be used as cocatalysts along with soluble or insoluble metal compounds as catalysts, optionally bound to high molecular weight carriers. The absorption liquid is at a pH of 3 to 10. The formaldehyde is condensed in situ in the absorption liquid optionally also in a reaction tube or cascade of stirrer vessels following the vessel containing the absorption liquid. Autocondensation of formaldehyde is stopped at a residual formaldehyde content in the reaction mixture of from 0 to 10% by weight by cooling and/or by inactivation of the catalyst with acids, and the catalyst is finally removed. For further details of this process, see German Offenlegungsschriften Nos. 2,721,093 and 2,721,186.

Formoses prepared in this way may also be subsequently converted into their hemiacetals with excess formaldehyde or α-methylolated by reaction with formaldehyde in the presence of bases.

The properties of the formoses can be varied within wide limits by controlling the formaldehyde condensation process. In general, the further the condensation reaction continues, i.e. the lower the residual formaldehyde content, the higher is the average molecular weight obtained and hence the hydroxyl functionality of the formoses. If the reaction is continued to a residual formaldehyde content of from 0 to 1.5% by weight, a formose containing approximately 25% by weight of components with 5 carbon atoms, 45% by weight of compounds with 6 carbon atoms and approximately 20% by weight of compounds with 7 or more carbon atoms is obtained. At the same time, a total of only about 10% of polyols, hydroxyketones and hydroxyaldehydes with 2, 3 and 4 carbon atoms is obtained. This corresponds to an average hydroxyl functionality of approximately 5.

Different proportions of components are obtained by stopping the formaldehyde condensation at somewhat higher residual formaldehyde contents. When the condensation reaction is stopped at a formaldehyde content of from about 2 to 2.5%, a mixture of polyvalent alcohols, hydroxyaldehydes and hydroxyketones having an average hydroxyl functionality of approximately 4 is obtained. Yet other proportions of components with a substantially lower average hydroxyl functionality are obtained when the condensation reaction is stopped at residual formaldehyde contents higher than 2.5.

In all of these processes, crossed Cannizzaro reactions between formaldehyde and the carbonyl groups of the formaldehyde condensation products take place to a considerable extent simultaneously with the autocondensation of formaldehyde hydrate. The formoses obtained contain a considerable quantity of polyhydric alcohols in addition to hydroxyaldehydes and hydroxyketones. This may be advantageous for many purposes, particularly when it is intended to hydrogenate the formoses into mixtures of polyhydric alcohols. For other purposes, however, for example for the production of highly flame-resistant polyurethane foams or the use of the formoses as substrates in the nutrient media of microorganisms, it is advantageous to obtain a formose containing as high a proportion of reducing sugars as possible, i.e. as little as possible of polyhydric alcohols formed by crossed Cannizzaro reactions. Moreover, the organic acids formed in the crossed Cannizzaro reaction (mainly formic acid with traces of acetic, lactic, glycollic and saccharic acids), are undesirable for many potential applications. They can only be removed from the reaction mixture by a relatively complicated procedure using anion exchangers.

DESCRIPTION OF THE INVENTION

It has now surprisingly been found that the crossed Cannizzaro reaction during the formation of formose can be significantly suppressed if certain tertiary amines are used to adjust the desired pH instead of inorganic bases, such as alkali metal or alkaline earth metal hydroxides which were previously used for this purpose. In contrast to these inorganic bases, such tertiary amines can easily be removed from the reaction mixture, e.g. by distillation. On the other hand, they may be left in the formoses if desired. In such a case they may serve as catalysts for a polyisocyanate polyaddition reaction in which the formoses are used as a reaction component to produce polyurethane resins. It has also been surprisingly found that when tertiary amines are used as the base, the pH during formaldehyde condensation is, in general, not critical. It may vary within relatively wide limits during the formation of formose, generally between 4.5 and 9, and preferably between 5 and 7.

The present invention thus relates to a process for the preparation of low molecular weight polyhydroxyl compounds by the autocondensation of formaldehyde hydrate in the presence of a soluble or insoluble compound of a metal of the 2nd to 4th Main Group or of the 2nd to 8th sub-Group of the Periodic System of Elements as catalyst, and optionally in the presence of compounds capable of enediol formation as cocatalysts and/or in the presence of low molecular weight and/or higher molecular weight polyhydroxyl compounds, wherein the pH during the condensation reaction is controlled by the addition of 5 to 200 milliequivalents, preferably 10 to 70 milliequivalents (per mol of formaldehyde), of a tertiary amine which contains an electrophilic hetero atom in the $\beta$-position to the tertiary nitrogen atom.

The use of amines, in general, is described in German Offenlegungsschriften Nos. 2,721,093 and 2,721,186 where formose is prepared directly from formaldehyde-containing synthesis gases. These references, however, do not disclose the specific amines used in the present invention.

It is surprisingly found that the suppression of the cross Cannizzaro reaction, which is the underlying purpose of this invention, occurs only if these tertiary amines are used. Primarily and Secondary amines behave much like inorganic bases in that they give rise to crossed Cannizzaro reaction to a substantial degree.

Tertiary amines which contain an electrophilic hetero atom in the $\beta$-position to the tertiary nitrogen atom include those with an additional tertiary nitrogen atom, a thioether group or, most preferably, an ether group. Examples of tertiary amines which may be used according to the invention include triethylene diamine, N,N'-dialkylpiperazines and N-alkylmorpholines, in each case with from 1 to 5, preferably 1 or 2, carbon atoms in the alkyl groups, N-phenylmorpholine, N-benzylmorpholine, 1,2-bis-morpholylethane and products of addition of ethylene oxide and/or propylene oxide to morpholine or piperazine with a molecular weight of up to about 2,000, preferably up to about 1,000. These compounds are particularly interesting for the purpose of this invention, as are also other basic polyethers already known for the production of polyurethanes such as the alkoxylation products of ammonia or primary or secondary monoamines or polyamines, because they can be left in the formose and later, if the formose is used as starting component for the production of polyurethane resins, they serve as catalysts which can be fixed in the molecule for the polyisocyanate polyaddition reaction.

According to the invention, the autocondensation of formaldehyde hydrate with the formation of hydroxyaldehydes and hydroxyketones is catalyzed by insoluble or, preferably, water-soluble compounds, in particular salts, of metals of the 2nd to 4th Main Group or 2nd to 8th sub-Group of the Periodic System of Elements. Ion exchanges charged with ions of these metals are also commercially particularly interesting for use as catalysts. According to the invention, the catalyst is generally used in quantities of about 0.01 to 10% by weight, preferably 0.05 to 5% by weight, most preferably 0.1 to 1% by weight, calculated as hydroxides of these metals and based on on the total quantity of reaction mixture. Metal hydroxides are less suitable as catalysts according to the invention because they favor the crossed Cannizzaro reaction. If metal hydroxides are to be used as catalysts, it is therefore advisable to use the smallest possible quantities of such catalysts, i.e. to work within the lower limit of the range indicated above. The catalysts used according to the invention are preferably formates, acetates, phenolates, thiophenolates, salicylates, carbonates or nitrates of the metals of the ion exchangers charged with metals already mentioned above. Compounds of divalent lead are particularly preferred catalysts according to the invention, especially lead acetate.

The autocondensation of formaldehyde hydrate is preferably carried out in the presence of compounds capable of enediol formation as cocatalysts. The compounds which are capable of enediol formation are generally used in quantities of from 0.1 to 50% by weight, preferably 1 to 20% by weight, most preferably 5 to 15% by weight, based on the quantity of formaldehyde. Any compounds which carry a hydroxyl group in the $\alpha$-position to a carbonyl group can in principle be used for this purpose. However, the preferred cocatalysts are formose itself and the oxidation products of polyhydric alcohols. In this connection, reference should be made to the literature references given above.

Instead of or in addition to the compounds which are capable of enediol formation, polyhydroxyl compounds may also be used in the process according to the invention in quantities of up to 200% by weight, preferably from 10 to 100% by weight, based on the quantity of formaldehyde used. The polyhydroxyl compounds described in German Offenlegungsschrift No. 2,714,104 and the polyols which are described hereinafter as starting components for the production of polyurethane resins may be used for this purpose.

As already mentioned above, when the condensation of formaldehyde hydrate is carried out in the presence of the above-described tertiary amines, the process conditions are not critical. Temperatures of from 10° to 150° C., preferably from 70° to 110° C., most preferably from 80° to 100° C. and a pH of preferably 4.5 to 9, most preferably 5 to 7, are generally employed. Aqueous alcoholic formalin solutions and/or aqueous paraformaldehyde dispersions containing from 10 to 70% by weight, preferably 20 to 65% by weight, most preferably 30 to 50% by weight of formaldehyde are generally used. The quantity of tertiary amine to be added depends on the acid content of the starting components but is generally between 5 and 200, preferably between 10 and 70 milliequivalents of tertiary nitrogen atoms per mol of formaldehyde. Very little acid is formed during the formation of formose due to the virtual suppression of the crossed Cannizzaro reactions. The pH falls only very slowly during this reaction. Thus, all of the tertiary amines may be added at the beginning of the condensation reaction. However, if reaction times are prolonged, as when very complete conversion of the formaldehyde is desired, crossed Cannizzrao reactions do take place to a slight extent. In such a case, it is advisable to add the tertiary amine portionwise or continuously. The reaction velocity can be influenced as desired by the method of adding the tertiary amine.

The process may also be carried out continuously, for example, in a cascade of stirred vessels. In this variation of the process, the residual formaldehyde content can be exactly adjusted by varying the residence time and pH in the individual stirred vessels. The proportions of components in the resulting formose can then easily be varied within wide limits and in a reproducible manner. The preparation of formose by the process according to the invention may be carried out equally conveniently and successfully in a continuously operated reaction tube in which the tertiary amine can be added continuously in the necessary quantities at one or more points along the tube so as to maintain the desired pH in the whole reaction volume. In this case, the proportions of components of the formose can again be varied within wide limits by varying the rates of flow through the tube and the pH.

The formose obtained according to the invention are valuable starting materials for numerous commercially interesting products. In particular, they are suitable for use as polyol components for the production of polyurethane resins.

The invention therefore also relates to a process for the production of a cellular or non-cellular polyurethane resin by the reaction of (A) polyisocyanates with
(B) low molecular weight polyhydroxyl compounds and, optionally
(C) higher molecular weight polyhydroxyl compounds, other chain lengthening agents, blowing agents, catalysts and other known additives,
wherein the substances used as component (B) are the formoses obtained according to the invention.

Suitable polyisocyanates for this purpose include, for example, the aliphatic, cycloaliphatic, araliphatic, aromatic or heterocyclic polyisocyanates such as those described, for example, by W. Siefken in Justus Liebigs Annalen der Chemie, 526, pages 75 to 136, for example, ethylene diisocyanate, tetramethylene-1,4-diisocyanate, hexamethylene-1,6-diisocyanate, dodecane-1,12-diisocyanate, cyclobutane-1,3-diisocyanate, cyclohexane-1,3- and 1,4-diisocyanate and any mixtures of these isomers, 1-isocyanato-3,3,5-trimethyl-5-isocyanatomethylcyclohexane as described in German Auslegeschrift No. 1,202,785 and U.S. Pat. No. 3,401,190, hexahydrotolylene-2,4-diisocyanate and -2,6-diisocyanate and any mixtures of these isomers, hexahydrophenylene-1,3-diisocyanate and/or 1,4-diisocyanate, perhydrodiphenylmethane-2,4'-diisocyanate, phenylene-1,3-diisocyanate and -1,4-diisocyanate, tolylene-2,4-diisocyanate and -2,6-diisocyanate and any mixtures of these isomers, diphenylmethane-2,4'-diisocyanate and/or 4,4'-diisocyanate, naphthylene-1,5-diisocyanate triphenylmethane-4,4',4''-triisocyanate, polyphenylpolymethylene polyisocyanates which can be obtained by aniline-formaldehyde condensation followed by phosgenation and which have been described, for example, in British Pat. Nos. 874,430 and 848,671, m- and p-isocyanatophenyl-sulphonyl isocyanates according to U.S. Pat. No. 3,454,606, perchlorinated aryl polyisocyanates such as those described for example, in German Auslegeschrift No. 1,157,601 and U.S. Pat. No. 3,277,138, polyisocyanates having carbodiimide groups as described in German Pat. No. 1,092,007 and U.S. Pat. No. 3,152,162, diisocyanates of the kind described in U.S. Pat. No. 3,492,330, polyisocyanates with allophanate groups as described e.g. in British Pat. No. 994,890, Belgian Pat. No. 761,626 and published Dutch Patent Application No. 7,102,524, polyisocyanates with isocyanurate groups, e.g. as described in U.S. Pat. No. 3,001,973, German Pat. Nos. 1,022,067 and 1,027,394, and German Offenlegungsschriften Nos. 1,929,034 and 2,004,048, polyisocyanates with urethane groups as described e.g. in Belgian Pat. No. 752,261, or U.S. Pat. No. 3,394,164, polyisocyanates with acylated urea groups according to German Pat. No. 1,230,778, polyisocyanates with biuret groups as described e.g. in German Pat. Nos. 3,124,605 and 3,201,372 and in British Pat. No. 889,050, polyisocyanates prepared by telomerization reactions as described for example, in U.S. Pat. No. 3,654,106, polyisocyanates with ester groups, such as those mentioned, for example, in British Pat. Nos. 965,474 and 1,072,956, U.S. Pat. No. 3,567,763, and German Pat. No. 1,231,688, reaction products of the above-mentioned isocyanates with acetals according to German Pat. No. 1,072,385 and polyisocyanates containing polymeric fatty acid groups according to U.S. Pat. No. 3,455,883.

The distillation residues obtained from the commercial production of isocyanates and still containing isocyanate groups may also be used, optionally as solutions in one or more of the above-mentioned polyisocyanates. Any mixtures of the above-mentioned polyisocyanates may also be used.

In general, it is particularly preferred to use commercially readily available polyisocyanates such as tolylene-2,4-diisocyanate and -2,6-diisocyanate and any mixtures of these isomers ("TDI"), polyphenylpolymethylene polyisocyanates of the kind which can be prepared by aniline formaldehyde condensation followed by phosgenation ("crude MDI"), and polyisocyanates containing carbodiimide groups, urethane groups, allophanate groups, isocyanurate groups, urea groups, or biuret groups ("modified polyisocyanates").

Suitable higher-molecular weight polyhydroxyl compounds especially those with a molecular weight of from 800 to 10,000, preferably 1,000 to 6,000, include e.g. polyesters, polyethers, polythioethers, polyacetals, polycarbonates and polyester amides having at least two, generally two to eight but preferably two to four hydroxyl groups, of the kind known per se for the production of both homogeneous and cellular polyurethanes.

Suitable polyesters with hydroxyl groups include e.g. reaction products of polyvalent, preferably divalent alcohols, to which trivalent alcohols may be added, and polyvalent, preferably divalent carboxylic acids. Instead of free polycarboxylic acids, the corresponding polycarboxylic acid anhydrides or corresponding polycarboxylic acid esters of lower alcohols or mixtures thereof may, of course, be used for preparing the polyesters. The polycarboxylic acids may be aliphatic, cycloaliphatic, aromatic and/or heterocyclic and they may be substituted, e.g. by halogen atoms, and/or may be unsaturated.

The following are mentioned as examples: Succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids such as oleic acid which may be mixed with monomeric fatty acids, dimethyl terephthalate and terephthalic acid bis-glycol esters.

The following are examples of suitable polyvalent alcohols: Ethylene glycol, propylene glycol-(1,2) and -(1,3), butylene glycol-(1,4) and -(2,3) hexanediol-(1,6) octanediol-(1,8) neopentylglycol, cyclohexanedimethanol (1,4-bis-hydroxymethylcyclohexane), 2-methyl-1,3-propanediol, glycerol, trimethylolpropane, hexanetriol-(1,2,6), butanetriol-(1,2,4), trimethylolethane, pentaerythritol, quinitol, mannitol and sorbitol, methylglycoside, diethylene glycol, triethylene glycol, tetraethylene glycol, polyethylene glycols, dipropylene glycol, polypropylene glycols, dibutylene glycol and polybutylene glycols. The polyesters may also contain a proportion of carboxyl end groups. Polyesters of lactones such as ϵ-caprolactone or hydroxycarboxylic acids such as ω-hydroxycaproic acid may also be used.

The polyethers used according to the invention which have at least two, generally two to eight and preferably two or three hydroxyl groups, are also known per se. They are prepared, for example, by polymerization of epoxides such as ethylene oxide, propylene oxide, butylene oxide, tetrahydrofuran, styrene oxide or epichlorohydrin, either each on its own, e.g. in the presence of boron trifluoride, or by addition of these epoxides, either as mixtures or successively, to starting components having reactive hydrogen atoms, such as water, alcohols, ammonia or amines. Examples of such starting compounds include ethylene glycol, propylene glycol-(1,3) or -(1,2), trimethylolpropane, 4,4'-dihydroxyl-diphenyl propane, aniline, ethanolamine or ethylene diamine. Sucrose polyethers may also be used according to the invention, e.g. those described in German Auslegeschriften Nos. 1,176,358 and 1,064,938. It is in many cases preferred to use polyethers which contain predominantly primary hydroxyl groups (up to 90% by weight, based on all the hydroxyl groups present in the polyether). Polyethers modified with vinyl polymers, e.g. the compounds obtained by polymerization of styrene or acrylonitrile in the presence of polyethers as described in U.S. Pat. Nos. 3,383,351, 3,304,273, 3,523,093 and 3,110,695 and German Pat. No. 1,152,536 are also suitable, as are polybutadienes which have hydroxyl groups.

Particularly useful polythioethers are the condensation products obtained by reacting thiodiglycol on its own and/or with other glycols, dicarboxylic acids, formaldehyde, aminocarboxylic acids or amino alcohols. The products obtained are polythio mixed ethers, polythio ether esters or polythio ether ester amides, depending on the cocomponents.

Suitable polyacetals include, for example, the compounds which can be prepared from glycols such as diethylene glycol, triethylene glycol, 4,4'-dioxethoxydiphenyl dimethylmethane, hexanediol and formaldehyde. Suitable polyacetals may also be prepared by the polymerization of cyclic acetals.

The polycarbonates with hydroxyl groups used may be of the known per se, for example, those which can be prepared by the reaction of diols such as propanediol-(1,3), butanediol-(1,4) and/or hexanediol-(1,6), diethylene glycol, triethylene glycol or tetraethylene glycol with diarylcarbonates, e.g. with diphenylcarbonate or phosgene.

Suitable polyester amides and polyamides include, for example, the predominantly linear condensates prepared from polyvalent saturated and unsaturated carboxylic acids or their anhydrides and polyvalent saturated and unsaturated amino alcohols, diamines, polyamines and mixtures thereof.

Polyhydroxyl compounds already containing urethane or urea groups and modified or unmodified natural polyols such as castor oil, carbohydrates or starch may also be used. Addition products of alkylene oxides and phenol formaldehyde resins or of alkylene oxides and urea formaldehyde resins are also suitable for the purpose of the invention.

Representatives of these compounds which may be used according to the invention have been described, for example, in High Polymers, Vol. XVI, "Polyurethanes, Chemistry and Technology" by Saunders-Frisch, Interscience Publishers, New York, London, Volume I, 1962, pages 32 to 42 and pages 44 to 54 and Volume II, 1964, pages 5 to 6 and 198 to 199 and in Kunststoff-Handbuch, Volume VII, Vieweg-Höchtlen, Carl-Hanser-Verlag, Munich, 1966, e.g. on pages 45 to 71.

Mixtures of the above-mentioned compounds which contain at least two isocyanate-reactive hydrogen atoms and have a molecular weight of from 800 to 10,000 may, of course, also be used; particularly, mixtures of polyethers and polyesters.

The starting components used according to the invention may also include compounds with a molecular weight of from 32 to 400 which have at least two isocyanate-reactive hydrogen atoms. These include compounds containing hydroxyl groups and/or amino groups and/or thiol groups and/or carboxyl groups, preferably hydroxyl groups and/or amino groups. They generally serve as chain lengthening agents or cross-linking agents. They generally have from two to eight isocyanate-reactive hydrogen atoms, preferably two or three such hydrogen atoms. The following are examples of such compounds: Ethylene glycol, propylene glycol-(1,2) and -(1,3), butylene glycol-(1,4) and -(2,3), pentanediol-(1,5), hexanediol-(1,6), octanediol-(1,8), neopentyl glycol, 1,4-bis-hydroxymethylcyclohexane, 2-methyl-1,3-propanediol, glycerol, trimethylolethane, pentaerythritol, quinitol, mannitol, and sorbitol, diethylene glycol, triethylene glycol, tetraethylene glycol, polyethylene glycols with a molecular weight of up to 400, dipropylene glycol, polypropylene glycols with a molecular weight of up to 400, dibutylene glycol, polybutylene glycols with a molecular weight of up to 400, 4,4'-dihydroxyl-diphenyl propane, dihydroxymethyl-hydroquinone, ethanolamine, diethanolamine, triethanolamine, 3-aminopropanol, ethylene diamine, 1,3-diaminopropane, 1-mercapto-3-aminopropane, 4-hydroxyphthalic acid, 4-aminophthalic acid, succinic acid, adipic acid, hydrazine, N,N-dimethylhydrazine, 4,4'-diaminodiphenylmethane, tolylenediamine, methylene-bis-chloroaniline, methylene-bis-anthranilic acid ester, diaminobenzoic acid ester and the isomeric chlorophenylenediamines.

According to the invention, polyhydroxyl compounds which contain high molecular weight polyadducts or polycondensates in a finely dispersed or dissolved form may also be used. Such modified polyhydroxyl compounds are obtained when polyaddition reactions (e.g. reactions between polyisocyanates and aminofunctional compounds) or polycondensation reactions (e.g. between formaldehyde and phenols and/or amines) are carried out in situ in the above-mentioned hydroxyl compounds. Processes of this kind have been described, for example, in German Auslegeschriften Nos. 1,168,075 and 1,260,142 and in German Offenlegungsschriften Nos. 2,324,134, 2,423,984, 2,512,385, 2,513,815, 2,550,796, 2,550,797, 2,550,833, and 2,550,862. These modified polyhydroxyl compounds can also be obtained according to U.S. Pat. No. 3,869,413 or German Offenlegungsschrift No. 2,550,860 by mixing a previously prepared aqueous polymer dispersion with a polyhydroxyl compound and then removing the water from the mixture.

When modified polyhydroxyl compounds of the kind mentioned above are used as starting components for the polyisocyanate polyaddition process, polyurethane resins with substantially improved mechanical properties are in many cases obtained.

When the polyhydroxyl compounds obtainable according to the invention are reacted on their own, i.e. without the addition of other isocyanate reactive components, with powerfully elasticizing polyisocyanates, e.g. polyisocyanates with a biuret structure as described in German Auslegeschrift No. 1,543,178, lightfast, scratch-resistant and solvent-resistant coatings and lacquers are obtained.

By alkoxylation, e.g. propoxylation and/or ethoxylation of formose, it is also possible to obtain polyether alcohols with a high functionality. Among these alcohols, those with high hydroxyl numbers are suitable for the manufacture of rigid or semirigid cellular polyurethane resins and those with low hydroxyl numbers as starting materials for highly flexible polyurethane foams.

Highly branched polyesters which can be used as additives for alkyd resins to improve their hardness can be synthesized by reacting the formoses prepared according to the invention with polybasic carboxylic acids of the kind mentioned above, e.g. phthalic acid, isophthalic acid, terephthalic acid, tetra- and hexahydrophthalic acid, adipic acid, or maleic acid by the usual methods of polyester condensation, for example as described in Houben-Weyl, Methoden der organischen Chemie, Vol. XIV 12, page 40. The hydroxyl polyesters synthesized from the hydroxyl compounds prepared according to the invention may, of course, also be used as starting components for the production of polyurethane resins.

Formoses prepared according to the invention are also readily reactable with long chain aliphatic monocarboxylic acids such as caprylic, capric, lauric, myristic, palmitic, stearic, oleic, linoleic, arachidonic or behenic acid and their derivatives, e.g. the methyl or ethyl esters or the anhydrides or mixed anhydrides, to produce hydroxyl containing esters. Like the ethoxylation products of the polyols or the carbamic acid esters obtained by reacting the polyhydroxyl compounds according to the invention with long chain monoisocyanates such as n-octyl, n-decyl, n-dodecyl, myristyl, cetyl or stearyl isocyanate (see e.g. K. Lindner, Tenside Volume III, Wissenschaftliche Verlagsgesellschaft Stuttgart, 1964, page 2336), these esters are non-ionogenic, surface active compounds which would be valuable emulsifiers, wetting agents or plasticizers.

The formoses according to the invention may also be used as moisturizers in cosmetics and synthetic resins but they may also be used for other purposes, e.g. as antifreezes. They may also be used as carbohydrate-containing substrates for the nutrient media of microorganisms. Those products which consists mainly of hydroxyaldehydes and hydroxyketones containing five and six carbon atoms have proved particularly suitable for this purpose.

The following Examples serve to explain the process according to the invention. The figures given are parts by weight of percentages by weight unless otherwise indicated.

EXAMPLES

Example 1

1,000 g (12.3 mol of formaldehyde) of a 37% aqueous formalin solution are heated to the reflux temperature together with 10 g (0.027 mol) of lead (II) acetate and 50 g of the cocatalyst described below. The heating bath is then removed and methylmorpholine is slowly added so that the mixture continues to boil. No formaldehyde can be detected after 20 minutes. The mixture is then cooled. Methylmorpholine consumption: 26 g.

After concentration by evaporation in a water jet vacuum, 373 g of a mixture of polyhydric alcohols, hydroxy aldehydes and hydroxyketones containing 1.8% of water are obtained. The mixture contains 80.4% of reducing constituents, calculated as glucose, and has a viscosity at 50° C. of 58,190 mPas and an OH number of 898.

The cocatalyst is prepared as follows:

3,000 parts of a 37% aqueous formaldehyde solution (37 mol of formaldehyde) are heated to 70°–90° C. 30 parts (0.08 mol) of lead (II) acetate are added at this temperature. The mixture is then heated to 100° C. and adjusted to pH 6.7 at this temperature by dropwise addition of a 15% $Ca(OH)_2$ suspension.

After 6 hours, the formaldehyde content has fallen to 20% and the addition of $Ca(OH)_2$ is stopped. The pH of the reaction mixture then slowly falls. When it has fallen to 5.7, the pH is kept constant at this level by further addition of $Ca(OH)_2$ suspension. After a further 7.5 hours, the residual formaldehyde content has fallen to 0.5% and the reaction mixture is cooled. An approximately 37% solution of a cocatalyst mixture consisting of hydroxyaldehydes and hydroxyketones is obtained. In this mixture, the molar ratio of compounds with 3 C atoms and compounds with 4 C atoms is 0.75, the molar ratio of compounds with 4 C atoms and compounds with 5 C atoms is 0.23 and the molar ratio of compounds with 5 C atoms and compounds with 6 C atoms is 0.67.

Example 2 (Comparison)

1,000 g (12.3 mol of formaldehyde) of a 37% aqueous formalin solution are heated to the reflux temperature together with 10 g (0.027 mol) of lead (II) acetate and 50 g of the cocatalyst from Example 1. The heating bath is then removed and piperidine is slowly added so that the mixture continues to boil. After 85 minutes, the residual formaldehyde content has fallen to 1.8%. The reaction is then stopped by cooling. Piperidine consumption: 58 g.

After concentration by evaporation in a water jet vacuum, 401 g of a mixture of polyhydric alcohols, hydroxyaldehydes and hydroxyketones containing 1.7% of water and containing 47.7% of reducing constituents, calculated as glucose, and having a viscosity of 21,565 mPas at 50° C. and an OH number of 668 are obtained.

This Example demonstrates that when a secondary amine is used, longer reaction times are required for formaldehyde condensation. Also, the consumption of base is higher and the yield of reducing sugars lower, both of these factors showing that Cannizzaro reactions take place to a considerable extent.

Example 3 (Comparison)

1,000 g (12.3 mol of formaldehyde) of a 37% aqueous formalin solution are heated to reflux temperature together with 10 g (0.027 mol) of lead (II) acetate and 50 g of the cocatalyst from Example 1. The heating bath is then removed and morpholine is slowly added so that the mixture continues to boil. After 45 minutes, the residual formaldehyde content has fallen to 2.7%. The reaction is then stopped by cooling. Morpholine consumption: 60 g.

After concentration in a water jet vacuum, 382 g of a mixture of polyhydric alcohols, hydroxyaldehydes and hydroxyketones containing 3.7% of water and containing 48.8% of reducing constituents, calculated as glucose, and having a viscosity at 50° C. of 1,379 mPas and an OH number of 611 are obtained.

Example 4 (Comparison)

1,000 g (12.3 mol of formaldehyde) of a 37% aqueous formalin solution are heated to the reflux temperature together with 10 g (0.027 mol) of lead (II) acetate and 50 parts of the cocatalyst from Example 1. The heating bath is then removed and 2-(2-aminoethylamino)-ethanol-1 is added slowly so that the mixture continues to boil. After 55 minutes at a pH of 5.7 to 6.2, the residual formaldehyde content has fallen to 3.3%. The reaction is stopped by cooling. Amine consumption: 68 g.

After concentration by evaporation under vacuum, 358 g of a mixture of polyhydric alcohols, hydroxyaldehydes and hydroxyketones containing 2.9% of water and containing 46.4% of reducing constituents, calculated as glucose, and having a viscosity at 50° C. of 3,069 mPas and an OH number of 70.3 are obtained.

Example 5

1000 g (12,3 mol of formaldehyde) of a 37% aqueous formalin solution are heated to reflux temperature together with 10 g (0,027 mol) of lead (II) acetate and 50 parts of the cocatalyst from example 1. The heating bath is then removed and dimethyl piperazine is added slowly so that the mixture continues to boil. After 18 minutes the total quantity of the formaldehyde has reacted. The reaction mixture is cooled to room temperature. Amine consumption: 30 g.

After concentration by evaporation under vacuum, 386 g of a mixture of polyhydric alcohols, hydroxyaldehydes and hydroxyketones containing 2,4% by weight of water and containing 78,6% of reducing constituents, calculated as glucose, and having a viscosity at 50° C. of 5917 mPas and an OH number of 903 are obtained.

Example 6

1000 g (12,3 mol of formaldehyde) of a 37% aqueous formalin solution are heated to the reflux temperature together with 10 g (0,027 mol) of lead (II) acetate and 50 parts of the cocatalyst from example 1. The heating bath is then removed and a 50% by weight aqueous solution of triethylene diamine is added slowly so that the mixture continues to boil. After 26 minutes the total quantity of the formaldehyde has reacted. The reaction mixture is cooled to room temperature. Amine consumption: 17 g. After concentration by evaporation under vacuum, 376 g of a mixture of polyhydric alcohols hydroxyaldehydes and hydroxyketones containing 1,3% by weight of water and containing 77,8% by weight of reducing constituents, calculated as glucose, and having a viscosity at 25° C. of 82186 mPas and an OH number of 912 are obtained.

What is claimed is:

1. In a process for the preparation of low molecular weight polyhydroxyl compounds wherein formaldehyde hydrate is condensed in the presence of soluble or insoluble compounds of metals of the 2nd to 4th Main Group or 2nd to 8th sub-Group of the Periodic System of Elements as catalyst, and optionally in the presence of compounds capable of enediol formation as cocatalyst and/or of low molecular weight and/or higher molecular weight polyhydroxyl compounds, the improvement which comprises controlling the pH during the condensation reaction by the addition of from 5 to 200 milliequivalents, based on 1 mol of formaldehyde, of N-methylmorpholine, N,N'-dimethylpiperazine or addition products, with a molecular weight of up to 1,000, of ethylene oxide and/or propylene oxide with morpholine or piperazine.

* * * * *